| United States Patent [19] | [11] Patent Number: 4,591,564 |
|---|---|
| Watson | [45] Date of Patent: May 27, 1986 |

[54] TRANSFERASE ENZYMES WHICH MODIFY THE 3'-TERMINI OF RIBONUCLEIC ACID AND METHODS

[75] Inventor: Kenneth F. Watson, Lolo, Mont.

[73] Assignee: The University of Montana, Missoula, Mont.

[21] Appl. No.: 440,602

[22] Filed: Nov. 10, 1982

[51] Int. Cl.$^4$ .......................... C12N 9/12; C12Q 1/68; C12P 19/34

[52] U.S. Cl. ........................................ 435/194; 435/6; 435/91; 536/27

[58] Field of Search ................................ 435/194, 199

[56] References Cited

U.S. PATENT DOCUMENTS

| | | | |
|---|---|---|---|
| 3,594,278 | 7/1971 | Naylor | 435/91 |
| 3,779,867 | 12/1973 | Katoh et al. | 435/91 |
| 3,796,631 | 3/1974 | Choay et al. | 435/91 |
| 3,849,249 | 11/1974 | Rokugawa et al. | 435/91 |
| 3,850,749 | 11/1974 | Kaufmann et al. | 435/91 |

OTHER PUBLICATIONS

Faras et al, Virology, vol. 58, 126–135 (1974).
Hargey et al, Chemical Abstracts 89: 102606g (1978).
Graevskaya et al, Chemical Abstracts 87: 116061w (1977).
Hagenbuchle et al, "Conservation of the Primary Structure at the 3' End of 18S rRNA from Eucaryotic Cells," *Cell*, vol. 13, p. 551 (1978).
Winter et al, "3' End Labelling of RNA with $^{32}$P Suitable for Rapid Gel Sequencing," *Nucleic Acids Research*, vol. 5, No. 9, p. 3129 (1978).

*Primary Examiner*—Lionel M. Shapiro
*Attorney, Agent, or Firm*—Lowe, Price, LeBlanc, Becker & Shur

[57] ABSTRACT

Three ribonucleotidyl terminal transferase enzymes are disclosed which modify the 3'-termini of ribonucleic acid (RNA) molecules by the addition of ribonucleotide units using ribonucleoside triphosphates as substrates. These terminal transferase activities are distinguishable by the specific ribonucleotide (e.g. AMP, CMP, or UMP) transferred to the 3'-hydroxyl terminus of an RNA primer. Also provided is a method for the 3'-terminal modification of RNA molecules by these enzymes and sequencing of RNA from its 3'-termini. The methods provide a convenient and efficient procedure for 3'-terminal modification (homopolymer tailing) of RNA required for synthesis of complete complementary DNA (cDNA) copies or double-stranded DNA gene copies by retrovirus-associated reverse transcriptase. Using the enzymes of the invention, RNA can also be radiolabelled to very high levels for molecular hybridization.

5 Claims, No Drawings

TRANSFERASE ENZYMES WHICH MODIFY THE 3'-TERMINI OF RIBONUCLEIC ACID AND METHODS

FIELD OF THE INVENTION

This invention relates to ribonucleotidyl terminal transferase enzymes which modify the 3'-termini of ribonucleic acid molecules by the addition of ribonucleotide units, and more particularly to three novel ribonucleotidyl terminal transferase enzymes which have the capability to selectively modify the 3'-terminus of ribonucleic acid molecules by the addition of adenosine-5'-monophosphate (AMP), cytidine-5'-monophosphate (CMP), or uridine-5'-monophosphate (UMP), and methods for their use in DNA synthesis and related areas.

BACKGROUND ART

Ribonucleotidyl terminal transferases have been described from a wide variety of organisms including bacteria [Paine and Boezi, J. Biol. Chem. 248, 4756 (1970); Sippel, Eur. J. Biochem. 37, 31 (1973)], lower eukaryots such as yeast [Haff and Keller, Biochem. Biophys. Res. Comm. 51, 704 (1973)], plants [Mans and Huff, J.Biol. Chem. 250, 3672 (1975); Brishammer and Juntti, Biochem. Biophys. Acta 383, 351 (1975)], and higher animals [Edmonds and Abrams, J. Biol. Chem. 235, 1142 (1960); Cory, et al., Biochem. Biophys. Res. Comm. 42, 778 (1971); Tsiapalis, et al., Biochem. Biophys. Res. Comm. 50, 737 (1973)]. There are riboadenylate terminal transferases specific for AMP addition [Paine and Boezi, J. Biol. Chem. 248, 4756 (1970)], those specific for CMP addition [Edmonds, J. Biol. Chem. 240, 4621 (1965)], those specific for GMP addition [Burkard and Keller, Proc. Nat. Acad. Sci., USA, 71, 389 (1974)], and those specific for UMP addition [Hozumi et al., Nature 256, 337 (1975)]. The riboadenylate terminal transferase activities from the bacteria, Escherichia coli, and from maize plants have been used for 3'-terminal modification of RNA prior to complementary DNA synthesis using reverse transcriptase [Hagenbuechle et al., Cell 13, 551 (1978)] and RNA sequencing [Winter and Brownlee, Nucl. Acids Res. 5, 3129 (1978)].

Ribonucleotidyl terminal transferases are enzymes which modify the 3'-termini of ribonucleic acids (RNA) by the addition of one or more ribonucleotides (CMP, UMP, AMP, or GMP) using ribonucleoside triphosphates (CTP, UTP, ATP, or GTP) as substrates. As mentioned above, such enzymes have been described from a variety of organisms including bacteria, lower eukaryots, plants, and higher animals.

Recent developments in recombinant DNA technology permit the replication and expression of genes from totally different biological classes in particular organisms. With the corresponding discovery of retrovirus reverse transcriptase (RNA-directed DNA polymerase), it is possible to synthesize DNA genes using RNA as template (nucleic acid to be copied) and a primer RNA or DNA molecule preferably hydrogen-bonded (base paired) to the 3'-terminal nucleotides of the RNA template. That some RNAs, specifically eukaryotic cellular messenger RNAs, have a 3'-homopolymer tail of adenylate residues facilitates initiation of synthesis of DNA complementary to the template RNA species at their 3'-termini using a complementary RNA or DNA primer such as oligo(rU) or oligo(dT). However, many other RNA species, of both cellular and viral origin, do not have such a 3'-homopolymer segment. Thus, synthesis of complete DNA gene copies of these RNA species by the above method is not directly possible unless the 3'-termini of such RNA molecules can be modified by the terminal addition of repeating units of a specific ribonucleotide to generate such a 3'-homopolymer tail. The present invention provides enzymes and methods which facilitate such RNA modification, thus making it possible to synthesize in vitro complete DNA copies of RNAs originally void of 3'-homopolymer sequences. Furthermore, one may select for the synthesis of a homopolymer stretch of adenylates, cytidylates, or uridylates.

SUMMARY OF THE INVENTION

It is, accordingly, one object of the present invention to provide a method for the isolation of three ribonucleotidyl terminal transferase enzymes which modify the 3' terminus of RNA molecules, whether or not they are originally void of 3'-homopolymer sequences.

It is a further object of the invention to provide a procedure for the simultaneous isolation of three ribonucleotidyl terminal transferase enzymes from cellular material.

A further object of the invention is to provide novel ribonucleotidyl terminal transferase enzymes which have been isolated from cellular material and which have the capacity to modify the 3' terminus of RNA molecules which are originally void of 3'-homopolymer sequences by the selective addition of AMP, CMP, or UMP monomer units.

A further object of the invention is to provide a method for the synthesis of complementary DNA and duplex DNA copies of 3'-modified RNA using retrovirus-associated reverse transcriptase and an appropriate homopolymeric primer.

A still further object of the present invention is to provide a method for the sequencing of ribonucleic acid from its 3'-hydroxyl terminus by the terminal addition of highly radioactive ribonucleotides or 3'-deoxyribonucleotide analogs.

Other objects and advantages of the present invention will become apparent as the description thereof proceeds.

In satisfaction of the foregoing objects and advantages, there is provided by this invention a method for the simultaneous isolation of three ribonucleotidyl terminal transferase enzymes, said enzymes having the capability of modifying the 3'terminus of ribonucleic acid molecules even when they are void of 3'-homopolymer sequences, by the addition of ribonucleotide units using ribonucleoside triphosphates as substrates. The method of isolation of the three ribonucleotidyl terminal transferases comprises: inoculation of chicks with avian myeloblastosis virus so that the chicks develop acute leukemia characterized by a high percentage of myeloblasts in the peripheral blood; removal of the blood and separation of the myeloblasts; sedimentation of the nuclei of the separated myeloblasts; treatment of the supernatant by protamine precipitation or cellulose anion exchange chromatography to remove soluble nucleic acids; separation of proteins; radioactive assay of column fractions to determine ribonucleotidyl terminal transferase activity; and further separation and purification of the fractions by salt precipitation, centrifugation, resuspension, and velocity gradient centrifugation; and recovering the terminal transferase enzymes.

Also provided is a method for the 3'modification of an RNA specie, and the synthesis of complementary and duplex DNA copies of the 3'-modified RNA by reverse transcription. The invention also provides for sequencing of ribonucleic acid from its 3' terminus after the selective stepwise addition of a ribonucleotide such as AMP, CMP, or UMP monomer unit or 3'-deoxynucleotide analog using one of the three ribonucleotidyl terminal transferase enzymes.

DESCRIPTION OF SPECIFIC EMBODIMENTS

As now known in the art, deoxyribonucleic acid (DNA) and ribonucleic acid (RNA) are the genetic information-carrying molecules of cells and viruses. DNA is formed by the polymerization of four "building-block" molecules called deoxyribonucleotides (denoted dC, dG, dA, dT). Similarly, RNA is constructed from four component ribonucleotides (denoted rC, rG, rA, rU). Unless such DNA or RNA chains are in circular form, they have ends or termini which are identified as the 5' (prime)-end and 3' (prime)-end.

Enzymes which modify the termini of nucleic acids (both RNA and DNA) are present in a wide variety of organisms (animals, plants, lower eukaryots such as yeast, and bacteria). The specificity of each enzyme dictates the modification of the 3' or 5' terminus of a DNA or RNA molecule. Thus, they are so named "ribo- or deoxyribonucleotidyl terminal transferases," because they transfer and link ribo- or deoxyribonucleotides to the end of a RNA or DNA molecule, respectively. Although the cellular function of this group of enzymes is essentially unknown, they have wide-spread applications in molecular biology.

In accordance with the present invention, three distinctly different ribonucleotidyl terminal transferase enzymes have been detected and fractionated from RNA tumor virus-infected chick immature blood cells. These enzymes are characterized primarily by the function they perform, rather than by specific physical properties. These enzymes each modify the 3'-terminus of RNA molecules with the transfer of UMP, CMP or AMP, respectively. Other ribonucleotides including 3'-deoxynucleotide analogs such as cordycepin-5'-monophosphate, may also be transferred. DNA does not serve as primer or template. They do not have an apparent specificity for any particular RNA specie, in that both cellular RNAs and viral RNAs serve as primers for the terminal addition reaction. Therefore, the primary distinction between the three enzymes resides in the specific ribonucleotide which the enzyme will transfer to the RNA molecule. These combined properties make it possible to add a limited number of rU, rC, or rA residues to the 3' ends of a broad spectrum of RNA molecules.

The number of ribonucleotides added to each RNA molecule is both a function of enzyme:RNA molar ratio in the reaction and the time of reaction. The pH optimum for all the enzyme activities is 8.2 and magnesium ion is much preferred as divalent cation (6-8mM). Ribonucleoside triphosphates are used as substrates rather than ribonucleoside diphosphates. The latter are required by another 3'-terminal modifying enzyme, polynucleotide phosphorylase [Grunberg-Manago and Ochoa, *J. Am. Chem. Soc.* 77, 3165 (1955)]. To serve as primer the RNA must have a free 3'-OH on the terminal nucleotide.

The transferase enzymes of this invention may be further characterized as having estimated molecular weights of 40,000 for the CMP and UMP active enzymes, and 56,000 for the AMP active enzyme; as retaining greater than 80% of their activity after four (4) to six (6) weeks storage in ice; and as having the capability to terminally modify ribonucleic acid even when they are void of 3'-homopolymer sequences.

The terminal transferases are produced from RNA tumor virus-infected chick blood cells. In general, this process comprises inoculating the chicks with avian myeloblastosis virus, inducing acute leukemia. The leukemia, when present, will be characterized by a high percentage of myeloblasts in the peripheral blood. The blood is then taken by heart puncture, usually with suction, and the white blood cells collected after centrifugation. Following washing in physiological saline buffer, the cells are then either taken directly for fractionation of the enzyme of interest, or frozen for later use.

The terminal transferase enzymes of the present invention and the resulting modified RNAs are useful in several areas. With the enzyme reverse transcriptase, the modified RNA molecules may be used as templates for the synthesis of complete complementary DNA copies and double-stranded DNA gene copies of cellular and viral RNA species which had no 3'-homopolymer tail site for initiation of DNA synthesis prior to modification. The availability of complementary DNA copies and double-stranded DNA gene copies of many RNA species (messenger RNA, ribosomal RNAs, transfer RNAs, and many viral RNAs to name a few) provides an extremely powerful tool for analyzing the structure, organization, and expression of viral and cellular genes. These DNA copies are particularly important in defining the initiation, coding, and termination sequences of messenger RNAs which is very important for expression of recombinant DNAs. They are also important as hybridization probes to search for, isolate, identify, and characterize corresponding genes present in chromosomal DNA. The double-stranded DNA gene copies are also valuable for cloning DNA copies of specific cellular and viral RNA sequences into hosts capable of more efficiently producing the gene products. This provides new procedures for a more detailed understanding of these cellular or viral genes, their structure, replication and expression, as well as providing simpler routes for development of medically- or health-related products such as antiviral vaccines. Direct utilization of the enzymes is available for sequencing RNA from its 3'-terminus by the terminal addition of very highly radioactive ribonucleotides or 3'-deoxyribonucleotide analogs such as cordycepin (3'-dATP) as substrate. This reaction is preferred to 3'-terminal labeling of RNA by bacteriophage T4 RNA ligase and pCp[5'-$^{32}$P] which requires long incubation (>3 hr), increasing the likelihood of ribonuclease degradation by contaminating enzymes. In addition, the enzymes may be used to prepare highly radiolabeled RNA molecules as probes for RNA-DNA hybridization experiments.

It will be understood, therefore, that the enzymes of this invention facilitate broadly a number of useful functions in modern biology, including synthesis of complete complementary DNA copies of selected RNA species with reverse transcriptase, further synthesis of complete double-strand DNA gene copies of selected RNA species, also with reverse transcriptase, RNA sequencing, and the preparation of highly radiolabeled RNA for molecular hybridization.

According to this invention, the three distinctly different ribonucleotidyl terminal transferases have been detected and fractionated from the RNA tumor virus-infected chick immature white blood cells. As pointed out, these enzymes each modify the 3' terminus of RNA molecules with the transfer of UMP, CMP or AMP, respectively. The enzymes do not have an apparent specificity for any particular RNA specie in that both cellular RNAs and viral RNAs serve as primers for the terminal addition reaction. Therefore, the primary distinction among the three enzymes resides in the specific ribonucleotide transferred to the RNA molecule. These combined properties make it possible to add a limited number of rU, rC, or rA residues to the 3' ends of any RNA molecules.

The ribonucleotidyl terminal transferases of this invention serve a number of useful functions in molecular biology, particularly in the areas of basic research related to recombinant DNA technology. Described below are several uses in this area for certain specific applications.

In one aspect, the synthesis of complete complementary DNA copies of selected RNA species can be performed with reverse transcriptase that is, by RNA-directed DNA polymerase. In this procedure, modification of any selected RNA species by the 3'-terminal addition of a specific ribonucleotide sequence provides a specific site at the 3'-end of the RNA for initiation of DNA synthesis by reverse transcriptase. These DNA copies of RNA can then be used as probes for the presence or synthesis of such RNA in a variety of studies. In addition, the DNA copies can be linked to a solid matrix and used in an affinity chromatography technique for preparation and isolation of large quantities of the RNA in question.

The most important aspect of interfacing the enzymes of this invention with this technique is that the modification occurs on the 3'-end of the RNA molecules and in no other position. To obtain complete complementary DNA copies of the RNA using reverse transcriptase, the synthesis of DNA must begin at the 3'-end of the RNA. This 3'-modification in association with an appropriately chosen primer for reverse transcriptase, assures initiation of DNA synthesis at the 3'-end of the RNA.

The enzymes can also be used for the synthesis of double-stranded DNA gene copies of selected RNA species with reverse transcriptase. Under conditions where double-stranded DNA synthesis is favorable, the RNA, terminally modified by any of the enzymes described herein, can direct the synthesis of a complete double-stranded DNA gene copy of the RNA. When the modified RNA is incubated with reverse transcriptase, a complementary homopolyribonucleotide primer attaches to the modified 3' RNA end, and a complementary DNA strand is synthesized. When this synthesis is complete, the reverse transcriptase, remaining in its enzyme-substrate complex, reverses its direction of synthesis, and commences construction of a DNA strand complementary to the newly created DNA strand, thereby forming the double-stranded DNA complex. This DNA can then be cloned by recombinant DNA techniques. These techniques include selection of a DNA vehicle or vector, joining the synthesized DNA to the vehicle, introducing the joined DNA into a host organism in which it can replicate, and screening for recombinant DNA replication as described, for example, in Cohen et al, *Proc. Nat. Acad. Sci. USA* 70, 3240 (1973). Many additional investigations and applications result from such manipulation.

RNA sequencing can also be conducted using the enzymes of this invention. Current methods of RNA sequencing require identifying either or both the 5'-and 3'-ends of the RNA molecules by radioactive tagging. While the 5'-termini of RNAs is quite easily labeled with [$^{32}$P] by an enzyme called polynucleotide kinase, a similar enzyme for tagging 3'-termini has not been described. Consequently, other less efficient methods have been employed. Using the terminal transferases described herein, any type of purified RNA molecule can be easily radiolabeled to very high levels (specific activity) at its 3'-terminus with a specific ribonucleotide (rU, rC, or rA) or a 3'-deoxyribonucleotide analog. Sequencing of the RNA can then be accomplished from the 3'-end of the molecule by methods known in the art [Winter and Brownlee, *Nucl. Acids Res.* 5, 3129 (1978); Donis-Keller, *Nucl. Acids Res.* 7, 179 (1979); Peattie, *Proc. Nat. Acad. Sci. USA* 76, 1760 (1979)].

The enzymes of the invention are also useful in the synthesis of very highly radioactive RNA for DNA/RNA hybridization experiments. The enzymes described can be used with $\alpha$[$^{32}$P] ribonucleoside triphosphate substrates to generate very high specific-activity RNA probes for DNA/RNA hybridization experiments. This is a very general technique applicable to numerous specific needs or requirements of researchers in the art.

The following examples are presented to illustrate the invention but are not to be considered as limiting thereon. In these examples, parts are by weight unless otherwise indicated. In the following examples are provided a procedure for the fractionation of three ribonucleotidyl terminal transferase enzymes from RNA tumor virus-infected avian myeloblast cells which modify the 3'-termini of ribonucleic acids (RNAs) by the specific stepwise addition of AMP, CMP, or UMP residues, respectively; and a procedure for 3'-terminal modification of RNA and its subsequent purification by affinity chromatography.

EXAMPLE I

Collection of cells. Ribonucleotidyl terminal transferase activities are present in RNA tumor virus-infected avian myeloblast cells. These cells are obtained by inoculation of one to three day-old chicks intravenously with avian myeloblastosis virus BAI strain A (Life Sciences, Inc., St. Petersburg, Fla.). Approximately 8–10 days post-inoculation, the chicks develop an acute leukemia with a large accumulation of immature white blood cells (myeloblasts) in the peripheral blood. The blood is taken by heart puncture with suction using heparin as an anticoagulant. The heparinized blood is centrifuged 15 min. at 800 xg and 4° C. resulting in the separation of red cells, immature white cells, and plasma containing virus. The white cells (virus-infected myeloblast cells) are suspended in a 50% (V/V) solution of chick serum and dilute mixture 199 (Microbiological Associates) and then centrifuged at 1,800 xg for 7 min. After discarding the supernatant, the cell pellet is washed two times with an equal volume of 0.9% (W/V) NaCl; 0.01M Tris, pH 7.4 and centrifuged as described above. After discarding the wash, the cells are used directly or stored at −20° C.

EXAMPLE II

Standard ribonucleotidyl terminal transferase assay. Reaction mixtures (50 μl) for assay of terminal transferase activity contain the following components: 50mM Tris, pH 8.2; 8mM MgCl$_2$; 1mM dithiothreitol (DTT); 200 μM of [$^3$H]-ATP, CTP, or UTP (specific activity 50–100 counts per min per pmol, International Chemical and Nuclear); 5–10 μg of RNA primer; and variable amounts (1–10 μl) of concentrated enzyme fraction. The reaction volume is mixed well in a small test tube, incubated at 37° C. for 30 min, and terminated by placing in an ice bath. Each reaction mixture is then spotted on a separate 2×2 cm disk of DE-81 paper (Whatman, Inc.) and washed six times with 5% (W/V) Na$_2$HPO$_4$ solution (3 ml of solution per paper disk) followed by two washes with glass-distilled water. The paper disks are dried and the radioactivity bound to the paper and representing terminal addition to RNA is determined in a liquid scintillation counter.

EXAMPLE III

RNA primer for terminal transferase assay. Any RNA may be used as primer for detection of terminal transferase activity provided it has a free 3'-hydroxyl group on its 3'-terminal nucleotide. Myeloblast cell RNA or *E. coli* RNA, isolated by conventional phenol extraction, are used routinely for detection of terminal transferase activity. RNA fractions may be pretreated with nuclease-free calf intestinal alkaline phosphatase [Efstratiadis, et al., *Nucl. Acids Res.* 4, 4165 (1977)]to maximize available 3'-hydroxyl termini, followed by phenol extraction to remove the phosphatase.

EXAMPLE IV

Fractionation of ribonucleotidyl terminal transferases. All enzyme fractionation steps are carried out at 0°–4° C. Twenty grams of packed, frozen cells are thawed, suspended in 20 ml of Buffer A (50 mM Tris, pH 7.4; 5mM MgCl$_2$; 0.5mM EDTA; and 1mM DTT and homogenized by 20 strokes in a Potter-Elvjhem homogenizer at 3,000 rpm or sonicated with 25 pulses at 225 watts on a Model W-350 Bronson sonifier. The homogenate is centrifuged 8 min. at 500 xg to sediment nuclei. The supernatant is further centrifuged 35 min. at 20,000 xg. The resulting supernatant is made 5% (V/V) with glycerol (final volume 35 ml) and a solution of protamine sulfate (5 mg per ml in water) is added with stirring to a level of 0.04 mg per A$_{260}$ unit of high speed supernatant. After 15 min., the suspension is centrifuged 15 min. at 20,000 xg. The protamine step is used to remove soluble nucleic acid from the supernatant. It may be substituted with DEAE-cellulose chromatography (a 1.5×20 cm column of Whatman DE-52 pre-equilibrated in 50mM Tris, pH 7.5). The enzyme activities do not bind to the DEAE-cellulose whereas nucleic acids bind under these conditions. The protamine sulfate supernatant or DEAE flow-through is chromatographed further by applying to a Sephadex CM-C-50 (K$^+$) cation-exchange column (1.5×20 cm) pre-equilibrated with 0.01M potassium phosphate, pH 8.0, containing 1mM DTT and 5% (V/V) glycerol. Following sample application, the column is washed with 0.01M potassium phosphate, pH 8 solution described above until all non-binding protein is washed through as determined by absorbancy at 280nm. The column is then washed stepwise with 0.11M potassium phosphate, pH 8 and 0.3M potassium phosphate, pH 8 solutions containing 1mM DTT and 5% (V/V) glycerol, collecting 1–2 ml fractions. To detect the presence of each ribonucleotidyl terminal transferase activity, 5–10 μl of column fractions is added to reaction mixtures as previously described containing an RNA primer and radiolabelled ATP, CTP, or UTP as substrate. Following incubation, the RNA is bound to the DE-81 paper, unincorporated radioactive substrate is washed away, and the amount of radioactivity bound to the paper disk is determined in a liquid scintillation spectrometer. This is a measure of the amount of AMP, CMP, or UMP terminally added to the RNA primer or terminal transferase activity.

Terminal transferase activities adding CMP and AMP residues to RNA are found in the 0.1M potassium phosphate elution of the cation exchange column. The activity adding UMP to the 3'-termini of RNA is recovered with the 0.3M potassium phosphate elution. Extensive washing of the column with 0.01M potassium phosphate solution after applying the sample removes an activity adding AMP residues. This activity has a strong preference for poly A as primer and may be distinct from the activity adding AMP residues to RNA.

The enzyme activities are pooled separately and concentrated by ammonium sulfate precipitation (70% saturation) at 0° C. After 30 min., the solutions are centrifuged 20 min. at 20,000 xg in clear plastic tubes using a swinging bucket rotor. The pellets are resuspended in up to 1 ml of 50mM Tris, pH 7.5; 1mM DTT; 10% (V/V) glycerol depending on the amount of protein precipitate. At this stage the activity adding UMP residues is essentially free of contaminating ribonuclease activity. The pool of activity adding CMP and AMP residues is further fractionated using phosphocellulose (Whatman P-11) chromatography at pH 7.2. The activities adding CMP and AMP residues are separated using a salt gradient elution (0.01M to 0.6M potassium chloride). After ammonium sulfate precipitation, the enzyme fractions are further purified by velocity gradient sedimentation on 10–30% glycerol gradients (12 ml) containing 50mM Tris, pH 7.5; 200mM NaCl; 1mM DTT. Up to 0.5 ml samples of enzyme are layered on the gradients and centrifuged 72 hr. at 4° C. and 40K rpm in a SW41 rotor (Beckman). The gradients are fractionated by needle puncture collecting 0.4 ml samples. Each fraction is then tested for the presence of terminal transferase activity specific for ATP, CTP, or UTP as substrate. The CMp- and UMP-incorporating activities both sediment with an estimated molecular weight of about 40,000. The AMP-specific activity is somewhat larger with an estimated molecular weight of 56,000. Further purification using hydroxylapatite chromatography (pH 6.8) has also been successful for necessary removal of ribonuclease contamination. This step is best employed prior to glycerol gradient centrifugation. Finally, pools are made of each activity and concentrated by ammonium sulfate precipitation (70% of saturation) at 0° C. After 60 min., the solutions are centrifuged 30 min. at 25,000 xg in clear plastic tubes using a swinging bucket rotor. The precipitates are drained well and resuspended in a small volume (0.1–0.3 ml) of 50 mM Tris, pH 7.5; 1mM DTT; and 10% (V/V) glycerol and stored in a capped tube in ice. Such enzyme fractions retain greater than 80% of their activity after 4–6 weeks. For longer storage, the glycerol content is increased to 50% (V/V) and the enzyme fractions are stored at −20° C. These three concentrated enzyme fractions provide activities dependent on RNA primer for 3'-terminal addition of specific ribonucleotides. Adding only one ribonucleoside triphosphate substrate to any reaction mixture assures the specific addition of only one kind of ribonucleotide, even if residual activity of one of the other terminal transferases is present.

EXAMPLE V

Preparation of RNA. Any RNA specie may be selected for modification. For example, only the 3'-terminal modification of E. coli 16S ribosomal RNA (rRNA) from 30S ribosomal subunits is described here. The 16S RNA may be obtained either by detergent-disruption of whole cells followed by SDS-phenol extraction and deoxyribonuclease treatment to remove DNA [Brawerman, in Methods in Enzymology 30, 605 1974)], or by SDS-phenol extraction of previously purified ribosomes [Hill, et al., J. Mol. Biol. 44, 263 (1969)]. In either case, the 16S rRNA is fractionated by centrifugation through 10-30% (V/V) glycerol gradients containing 10 mM Tris.HCl (pH 7.4), 40mM LiCl, 5mM EDTA, and 0.2% (W/V) SDS for 8 hr. at 21° C. and 40,000 rpm using a Beckman SW41 rotor. Gradient fractions (0.4 ml) are collected from the bottom of the tube by needle puncture and the absorbancy at 260 nm is determined. The 16S rRNA is pooled and concentrated by precipitation with 2 volumes of ethanol in the presence of 0.2M NaCl. To assure the intactness of the 16S rRNA, it is denatured with dimethylsulfoxide (DMSO) and subjected to DMSO-sucrose gradient centrifugation for 36 hr. at 20° C. and 54,000 rpm using a Beckman SW60 rotor. Peak fractions of 16S rRNA are pooled and stored at −20° C. as a precipitate in 66% ethanol and 0.2M NaCl. Prior to use, the required amount of RNA is collected by centrifugation for 20 min. at −5° C. and 20,000 xg using a swinging bucket rotor. After washing the RNA pellet twice with 70% ethanol solution followed by centrifugation for 5 min. at 20,000 xg, residual ethanol is aspirated and the RNA is resuspended in 0.01M Tris.HCl (pH 7.4), 0.1mM EDTA, 0.1M NaCl at a concentration of 2 mg per ml (20 $A_{260}$ units per mg). To provide maximally available 3'-OH RNA termini, treatment with calf intestinal alkaline phosphatase followed by SDS-phenol extraction is suggested. This step should be performed prior to the final DMSO-sucrose gradient centrifugation treatment.

EXAMPLE VI

Modification of 3'-termini of 16S rRNA by ribonucleotidyl terminal transferase. In a final reaction volume of 0.1 ml containing 50mM Tris.HCl (pH 8.2), 6-8mM $MgCl_2$, 1mM DTT, and 0.2mM of [$^3$H]CTP (specific activity 100 counts per min per pmol), add 10 μg of 16S rRNA (20 pmol of 3'—OH termini) sufficient units of terminal transferase to add 20 pmol of nucleotide per pmol of 3'—OH termini. One unit of terminal transferase is that amount of enzyme necessary to incorporate 1 pmol of nucleotide per minute per pmol of 3'—OH termini. To minimize the time necessary to accomplish the modification as described above a constant amount of any selected RNA should be titrated with increasing enzyme prior to modification to assure enzyme excess.

EXAMPLE VII

Fractionation of 3'-terminally modified 16S rRNA from the reaction mixture. Following incubation of the 16S rRNA with the terminal transferase adding cytidylate residues to the 3'-termini, the reaction mixture is terminated with the addition of SDS and EDTA to 1% and 10mM, respectively, and phenol extracted. Following G-50 Sephadex chromatography to remove unincorporated substrate (1.5×30 cm column) using 10mM Tris.HCl (pH 7.4), 40mM LiCl, 1mM EDTA, and 0.2% SDS as chromatography buffer solution, the 16S rRNA in the excluded volume is concentrated by precipitation with 2 volumes of ethanol and 0.2M NaCl at −20° C. overnight. Following centrifugation to collect the 16S rRNA, it is resuspended in 10mM Tris.HCl (pH 7.4), 1mM EDTA, and 0.2% SDS, and heated at 80° C. for 3 min. with quick cooling. After the addition of NaCl solution to a final concentration of 0.5M, the sample of rRNA is chromatographed on oligo(dI)-cellulose (Collaborative Research, Inc.). Only 16S rRNA containing the 3'-tail of CMP residues will form rC-dI hybrids and bind to the column in high salt. Unmodified RNA passes through the column. 16S rRNA bound to the column is eluted with 10mM Tris (pH 7.4), 1mM EDTA, 0.2% SDS buffer. Its presence is detected by radio-activity and $A_{260}$ absorbancy. The peak of RNA is concentrated by ethanol precipitation as described above and stored at −20° C. This procedure not only selects for the 3'-modified RNA but also provides a means to determine the percentage of 16S rRNA molecules modified. Knowing the mass of RNA present as a function of absorbance at 260 nm and the amount and specific activity of radioactivity in 3'-RNA tails, an average length of tails may be calculated.

It will be understood that modification of the 3'-termini of a RNA specie may also be accomplished by the addition of AMP units or UMP units depending on which enzyme is employed. These 3'-modified RNAs may be purified finally using oligo(dT)-cellulose or oligo(dA)-cellulose chromatographies, respectively. For further reverse transcription of these 3'-modified RNAs, oligo(rI) or oligo(dG) is the preferred primer for 3'-CMP tailed RNA; oligo(rU) or oligo(dT) for 3'-AMP tailed RNA; and oligo(rA) or oligo(dA) for 3'-UMP tailed RNA. The ribonucleotide primers are most useful for synthesis of double-stranded DNA copies of RNA by reverse transcriptase [Watson, et al., Biochemistry 18, 3210 ( 1979)].

The invention has been described with respect to certain preferred embodiments. However, as obvious variations thereon will become apparent to those skilled in the art, the invention is not to be limited thereto.

What is claimed is:

1. A method for the isolation of three ribonucleotidyl terminal transferase enzymes, said enzymes having the capability of modifying the 3' terminus of ribonucleic acid molecules by the addition of ribonucleotide units using ribonucleotide triphosphates as substrates, said method comprising:
    (a) injecting of chicks with avian myeloblastosis virus so that the chicks develop acute leukemia characterized by a high percentage of myeloblasts in the peripheral blood;
    (b) removing the blood and isolating the myeloblasts;
    (c) eliminating the myeloblasts' nuclei;
    (d) separating and fractionating proteins;
    (f) determining enzyme activity, and
    (g) recovering the terminal transferase enzymes.

2. A method according to claim 1 comprising the steps of:
    (a) inoculation of chicks with avain myeloblastosis virus so that the chicks develop acute leukemia characterized by a high percentage of myeloblasts in the peripheral blood;

(b) removal of the blood and separation of the myeloblasts by centrifugation and washing;

(c) sedimentation of the nuclei of the separated myeloblasts by homogenization or sonication and centrifugation;

(d) treatment of the supernatant by a protamine precipitation or DEAE-cellulose chromatography to remove soluble nucleic acids;

(e) separation of proteins by cation exchange chromatographies;

(f) radioactive assay of column fractions to determine ribonucleotidyl terminal transferase activity;

(g) further separation and purification of the fractions by precipitation, centrifugation, resuspension, and velocity gradient centrifugation; and (h) recovering the terminal transferase enzymes.

3. A method according to claim 1 wherein the enzyme modifies the 3' terminus of ribonucleic acid with the transfer of uridine-5' monophosphate.

4. A method according to claim 1 wherein the enzyme modifies the 3' terminus of ribonucleic acid with the transfer of cytidine-5'-monophosphate.

5. A method according to claim 1 wherein the enzyme modifies the 3' terminus of ribonucleic acid with the transfer of adenosine-5'-monophosphate.

* * * * *